July 24, 1951 H. C. SWIM Plant Pat. 1,023
NECTARINE PLANT
Filed June 14, 1950
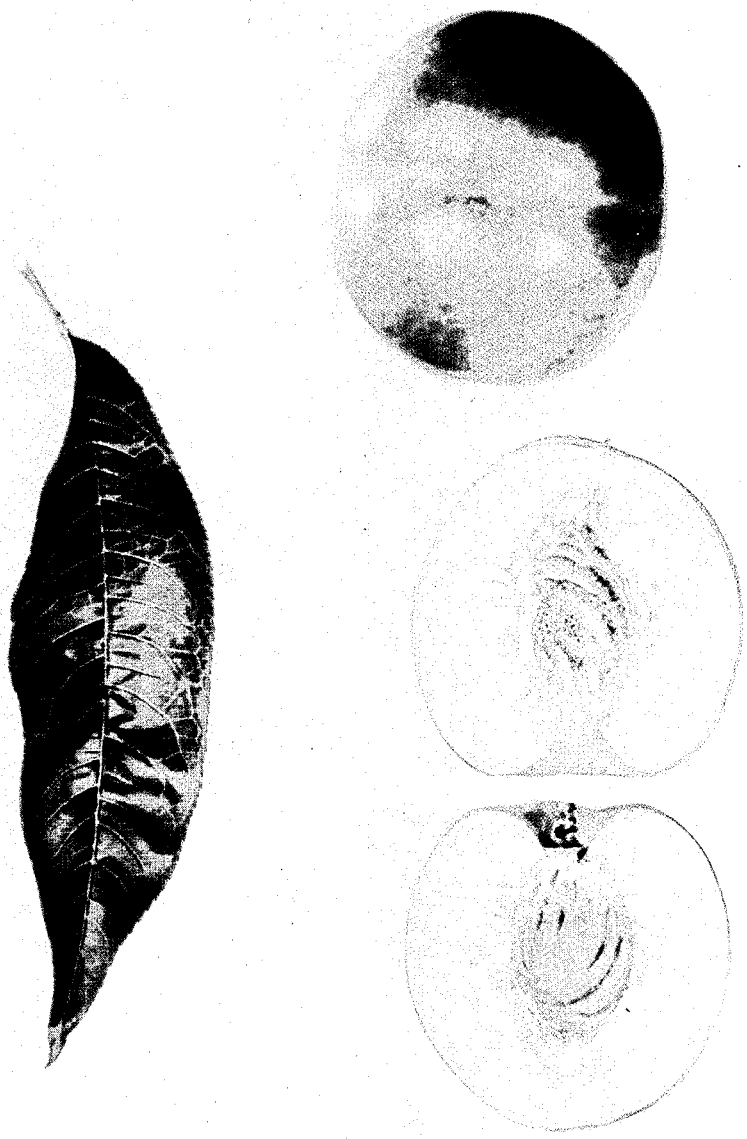
Inventor.
H. C. Swim
By: Robb & Robb
Attorneys.

Patented July 24, 1951

Plant Pat. 1,023

UNITED STATES PATENT OFFICE 1,023

NECTARINE PLANT

Herbert C. Swim, Ontario, Calif., assignor to Armstrong Nurseries, Inc., Ontario, Calif., a corporation of California Application June 14, 1950, Serial No. 167,940

1 Claim. (Cl. 47—62)

The present invention relates to a new and distinct variety of nectarine plant, originated from seed resulting from hand pollination of a first generation seedling of "Goldmine" nectarine (unpatented) × "Rio Oso Gem" peach (Plant Patent No. 84), with pollen from a first generation seedling of "Goldmine" nectarine × "July Elberta" peach (Plant Patent No. 15).

In features of novelty and distinctiveness, the above noted breeding has produced a fruit tree, the characteristics of which are unlike any other known variety of nectarine in commerce today, and the combination of the following characteristics make this new variety stand out from all others in important respects:

(1) An early ripening season in a subtropical climate characterized by an average of 600 hours of temperatures 40° F. or less each winter, which to my knowledge is earlier than any other variety available in commerce;

(2) A fruit which is white-fleshed and freestone, with high skin color as hereinafter more specifically described;

(3) A tree with a short dormancy requirement such as to insure annual production in subtropical zones; and (4) Leaves characterized as to conformation by the classification of wavy and crinkled, where samples 6 inches or more in length taken from the middle of a branch are used. (This classification terminology is in accordance with that set up by Meader and Blake in "Identification of Peach Varieties," Proceedings of the American Society for Horticultural Science, 1939, volume 37, pages 203–206.)

This new variety differs from its parent varieties in that it is a nectarine, whereas both parents were peaches, both of which, however, were genetically heterozygous for nectarine. It is most similar in appearance and climatic adaptation to the variety "Goldmine," which is also a white-fleshed freestone, but it is more highly colored on the skin and ripens fully six weeks earlier, and has a substantially shorter dormancy requirement than "Goldmine." It is similar in breeding background to the variety "Pioneer" (Plant Patent No. 787), but is white-fleshed, whereas "Pioneer" is yellow-fleshed, and its fruit ripens approximately one month earlier than that of "Pioneer," and has a shorter dormancy requirement, making it suited to a climate even more moderate than that suited to "Pioneer."

Asexual reproduction of the new variety by budding at Ontario, California, shows that the foregoing characteristics come true to form and are established and transmitted through succeeding propagations.

The accompanying drawing shows specimens of the foliage and fruit of this new nectarine tree, with the fruit in elevation and also in section, with and without the pit.

The following is a detailed description of the new variety, based upon observations of specimens grown at Ontario, California, with color terminology according to Robert F. Wilson's Horticultural Colour Chart, with exceptions as noted from Ridgway's Color Standards and Nomenclature:

Dates of first and last picking: Varies somewhat from year to year because of variable winter chilling in Southern California but usually ripens during the last week in June or the first week in July; occasionally ripens as early as mid-June and as late as mid-July. Picking period—10 days.

*Tree*

Large size; vigorous; upright; spreading; more or less dense; somewhat vase formed; productive to medium productive; regular bearer.

Trunk: Medium stocky; moderately smooth.

Branches: Medium stocky; moderately smooth; glossy.

*Color.*—Color of one year old branch (1 cm. dia.): Bark is basically Warm Sepia, Plate XXIX (Ridgway), mostly overlaid with thin outer layer of Smoke Gray, Plate XLVI (Ridgway). Where more exposed to sun the color approaches Saccardo's Umber, Plate XXIX (Ridgway).

*Lenticels.*—Medium in number; medium size.

Leaves (mature):

*Length.*—13–16 cm.

*Width.*—3–4.5 cm. Large; acuminate; lanceolate; moderately thick.

*Color.*—Upper surface—near Cress Green, Plate XXXI (Ridgway). Lower surface—near Asphodel Green, Plate XLI (Ridgway). Midrib—near Chrysolite Green, Plate XXXI (Ridgway).

*Leaf conformation.*—Usually somewhat wavy and crinkled along midrib; sometimes smooth, however.

*Margin.*—Glandular; finely serrate.

*Petiole.*—Medium length: 9 to 11 mm.; moderately thick.

*Glands.*—Average number, 2 to 7; some opposite; mostly alternate; medium size; reniform. Color—near Kildare Green, Plate XXXI (Ridgway). Sometimes tinged with Pecan Brown, Plate XXVIII (Ridgway). Position—near base of leaf on upper half of petiole; occasionally on the base of the leaf blade.

*Stipules.*—Early deciduous; 5 to 7 mm. in length; narrow with pointed apex; long irregular glandular teeth on the margins.

Flower buds: Free portions of the calyx are pubescent. Before the petals unfold the pistil usually protrudes and finally many of the stamens also protrude before the petals unfold. Length of bud as petals begin to unfold, 15–18 mm. Plump.

Flowers: Non-showy, 20–25 mm. in diameter. 40–50 filaments, usually all with anthers and pollen. A single row of usually 5 petals. Petals nearly oval in shape, 10 to 12 mm. long and 7 to 8 mm. wide at the widest portion. Color of petal as flower opens near Neyron Rose, Plate 623/3, page 76, turning to near Neyron Rose, Plate 623/1, page 76, in the aged flower especially in the basal region. Filaments near white as the flower opens becoming near Spiraea Red, Plate 025/1, page 112, in color at the time the petals fall.

*Dates first and full bloom.*—First bloom—first week in March. Full bloom—mid-March. Early compared with other varieties.

*Fruit*

Maturity when described—eating hard ripe. Date, July 15, 1949.

Size: Somewhat variable; medium size. With moderate thinning: Diameter, axial, 2 to 2¼ inches. Transverse in suture plane, 2 to 2¼ inches. At right angles to suture plane, 2 to 2¼ inches.

Form: Somewhat variable; symmetrical; broadly ovoid.

*Suture.*—Distinct but shallow; extends from base to beyond apex over 75% of circumference; has slight depression on both sides of pistil point.

*Ventral surface.*—Rounded, slightly lipped toward apex. Lips—equal.

*Stem cavity.*—Rounded with suture showing on one side. Depth—⅜ inch. Breadth—⅝ inch. Markings—suture more distinct in stem cavity.

*Base.*—Rounded to truncate; slight transverse depression caused by branch to which stem is joined.

*Apex.*—Rounded; somewhat depressed. Pistil point in depression—apical.

Stem: Length, ¼ inch; medium to stout; glabrous. Adherence to stone—strong to medium.

Skin: Medium thick; medium tough; somewhat tenacious to flesh. Tendency to crack—none in wet or dry season.

*Color.*—At base and where quite shaded near Pod Green, Plate 061/2, page 120, shading into Mimosa Yellow, Plate 602/2, page 143. Otherwise near Delft Rose, Plate 020, page 108, becoming Ruby Red, Plate 827, page 171, where very much exposed to the sun.

Flesh:

*Color.*—White. Surface of pit cavity—white, with occasional flecks of Currant Red, Plate 821/3, page 167.

*Juice.*—Abundant; sweet.

*Texture.*—Firm; medium crisp; melting.

*Fibres.*—Few; coarse; tender.

*Ripens.*—Evenly.

*Flavor.*—Subacid; mild.

*Aroma.*—Distinct.

*Eating quality.*—Good.

Stone: Free; fibres short; retains short fibre-like threads along dorsal ridge.

*Size.*—Medium to small; length, 1 to 1⅛ inches; breadth, ¾ to ⅞ inches; thickness, ½ to ⅝ inches.

*Form.*—Obovoid.

*Base.*—Straight. Hilum — oval. Apex — cuspidate.

*Sides.*—Equal. Surface — irregularly furrowed near apex; ridged near apex; pitted toward base.

*Ridges.*—Rounded.

*Pits.* — Elongated. Ventral edge — thick, without wing throughout.

*Dorsal edge.*—Narrow with shallow groove to above center. Ridges on either side interrupted.

*Color of stone.*—Between Cinnamon and Sayal Brown, Plate XXIX (Ridgway); flecked with Currant Red, Plate 821/3, page 167, near base and along dorsal edge.

*Tendency to split.*—None.

Use: Market; local; excellent for dessert.

Keeping quality: Good.

Resistance to:

*Insects.*—Good to medium.

*Diseases.*—Good.

Shipping quality: Good.

I claim:

A new and distinct variety of nectarine plant, characterized as to novelty by its early ripening season in subtropical climates, by its white-fleshed and freestone fruit with high skin color, by its short dormancy requirement, and by its wavy and crinkled leaves, substantially as shown and described.

HERBERT C. SWIM.

No references cited.